(12) United States Patent
Logrippo

(10) Patent No.: US 11,285,086 B2
(45) Date of Patent: Mar. 29, 2022

(54) METHOD FOR MAKING AN ACID ETCHED CANNABINOID MOLECULE BATH BOMB

(71) Applicant: Heather Louise Logrippo, Shrewsbury, MA (US)

(72) Inventor: Heather Louise Logrippo, Shrewsbury, MA (US)

( * ) Notice: Subject to any disclaimer, the term of this patent is extended or adjusted under 35 U.S.C. 154(b) by 0 days.

(21) Appl. No.: 15/996,346

(22) Filed: Jun. 1, 2018

(65) Prior Publication Data

US 2018/0271754 A1 Sep. 27, 2018

(51) Int. Cl.
*A61K 8/02* (2006.01)
*A61K 8/49* (2006.01)
*A61K 8/365* (2006.01)
*A61K 8/92* (2006.01)
*A61K 8/20* (2006.01)

(52) U.S. Cl.
CPC ............ *A61K 8/022* (2013.01); *A61K 8/20* (2013.01); *A61K 8/365* (2013.01); *A61K 8/498* (2013.01); *A61K 8/922* (2013.01); *A61K 2800/805* (2013.01)

(58) Field of Classification Search
CPC .......... A61K 8/022; A61K 8/20; A61K 8/365; A61K 8/498; A61K 8/676; A61K 8/922; A61K 2800/805; A61Q 19/10
See application file for complete search history.

(56) References Cited

U.S. PATENT DOCUMENTS

| 8,642,645 B2 * | 2/2014 | Kelly | A61K 31/194 |
| | | | 424/195.15 |
| 2017/0266127 A1* | 9/2017 | Denniston | A61K 31/05 |
| 2018/0147179 A1* | 5/2018 | Raber | A61K 31/352 |

OTHER PUBLICATIONS

Kalmanovitch, Michael, "Homemade Bath Bombs", Earth's General Store, 2016, obtained from the internet at https://earthsgeneralstore.ca/homemade-bath-bombs/ (Year: 2016).*

Kush Queen, Apr. 2018, obtained from the internet at https://www.kushqueencannabis.com/bath-bombs-1 (Year: 2018).*

* cited by examiner

*Primary Examiner* — Mina Haghighatian
*Assistant Examiner* — Nathan W Schlientz
(74) *Attorney, Agent, or Firm* — Behmke Innovation Group, LLC; George P. Kobler

(57) ABSTRACT

Method for making a Cannabinoid molecule bath bomb by first etching the surface of at least one of Δ9 Tetrahydrocannabinol molecule and Cannabidiol molecule. The etched Cannabinoid molecule is then combined with Sodium Bicarbonate, Citric acid, Magnesium Chloride, and a viscous binder. Once the ingredients have been combined the resulting mixture is dried to form a Cannabinoid molecule bath bomb.

4 Claims, 5 Drawing Sheets

100 # METHOD FOR MAKING AN ACID ETCHED CANNABINOID MOLECULE BATH BOMB

BACKGROUND

There are many forms of bath bombs, including the rapidly growing market for bath bombs made with molecules from *Cannabis Sativa* and *Cannabis Indica*. The most commonly sought after molecules are Δ9 tetrahydrocannabinol and Cannabidiol. However many of the products on the market are more focused on the novelty of the use of a Cannabinoid molecule, rather than on the pharmacological effects of the bath bomb.

Cannabinoid molecules affect cannabinoid receptors ($CB_1$ and $CB_2$) in human cells. Δ9 tetrahydrocannabinol (THC) is the main psychoactive Cannabinoid molecule found in *Cannabis Sativa* and *Cannabis Indica*. THC operates as an agonist to $CB_1$ and $CB_2$. THC can exist in a decarboxylated form which is extremely psychoactive in humans, or in a non-decarboxylated form. Cannabidiol (CBD) is not psychoactive and operates as an inverse-agonist to $CB_1$ and $CB_2$.

Prior literature such as United States Patent Application Publication No. 2012/0295968 A1, published Nov. 22, 2012, suggests that CBD and THC can have positive pharmacological effects when used as pills, nasal sprays, capsules, syrups, eye drops, and topical salves.

Cannabinoid bath bombs have suffered from reduced pharmacological effects, because the Cannabinoid molecules have been merely added in as a novelty or selling point. These novelty bath bombs suffer because the Cannabinoid molecule is not properly exposed. Further, simply mixing Cannabinoid molecules into the rest of the bath bomb composition during formation is not pharmacologically effective.

BRIEF DESCRIPTION OF THE DRAWINGS

Several alternative embodiments will hereinafter be described in conjunction with the appended drawings and figures, wherein like numerals denote like elements, and in which.

DETAILED DESCRIPTION

Figure 1:
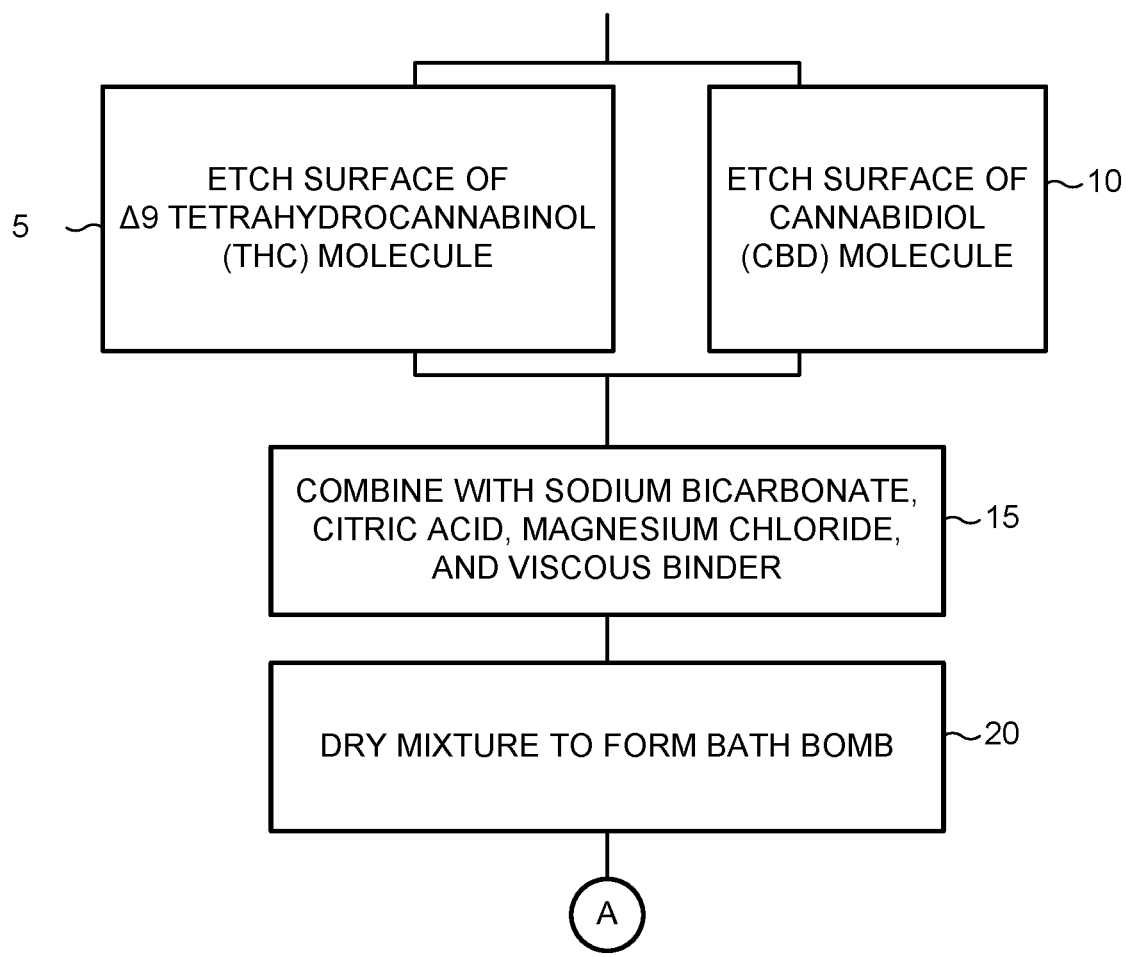
FIG. 1 is a flow diagram that depicts one example method for making a Cannabinoid molecule bath bomb.

FIG. 1 is a flow diagram that depicts one example method for making a Cannabinoid molecule bath bomb. In the interest of clarity, several example alternative methods are described in plain language. Such plain language descriptions of the various steps included in a particular method allow for easier comprehension and a more fluid description of a claimed method and its application. Accordingly, specific method steps are identified by the term "step" followed by a numeric reference to a flow diagram presented in the figures, e.g. (step 5). All such method "steps" are intended to be included in an open-ended enumeration of steps included in a particular claimed method. For example, the phrase "according to this example method, the item is processed using A" is to be given the meaning of "the present method includes step A, which is used to process the item". All variations of such natural language descriptions of method steps are to be afforded this same open-ended enumeration of a step included in a particular claimed method.

Also, unless specifically taught to the contrary, method steps are interchangeable and specific sequences may be varied according to various alternatives contemplated. Accordingly, the claims are to be construed within such structure.

FIG. 1 further illustrates that this example method also includes a step wherein the surface of a Δ9 Tetrahydrocannabinol (THC) molecule is etched (step 5). The present example method also comprises a step wherein the surface of a Cannabidiol (CBD) molecule is etched (step 10). Applicant is aware of at least 113 identified molecules in *cannabis*, of which THC and CBD are the most commonly known and sought. It should be appreciated that when the THC or CBD molecule are etched, they are more properly exposed and provide enhanced pharmacological effects.

The present method further comprises a step wherein the acid-Cannabinoid molecule is combined with Sodium Bicarbonate, Citric acid, Magnesium Chloride, and a viscous binder (step 15). It should be appreciated that the use of Magnesium Chloride improves the pharmacological effect of the resulting Cannabinoid molecule bath bomb as herein described. Magnesium Chloride easily passes through the skin when used topically and serves as a carrier thereby enhancing transdermal absorption of at least one of the etched THC molecule and the etched CBD molecule. Further, Magnesium Chloride can act as a carrier, bringing along other molecules and minerals through the skin. FIG. 1 further depicts that the present example method also includes a step wherein the resulting mixture is dried to form a bath bomb (step 20).

According to one illustrative use case, the Cannabinoid molecule bath bomb is placed in a container of water, commonly a bath tub. As the Cannabinoid molecule bath bomb is saturated the Sodium Bicarbonate activates with the Citric acid powder to create Carbon Dioxide. This released Carbon Dioxide causes the water in the container to "fizz" and bubble. This bubbling action is sought after to provide a pleasant and relaxing experience for the user. It should be appreciated that very little liquid is used in the creation of a Cannabinoid molecule bath bomb, in order to prevent the Sodium Bicarbonate powder and Citric acid powder from reacting together prematurely.

Figure 2:
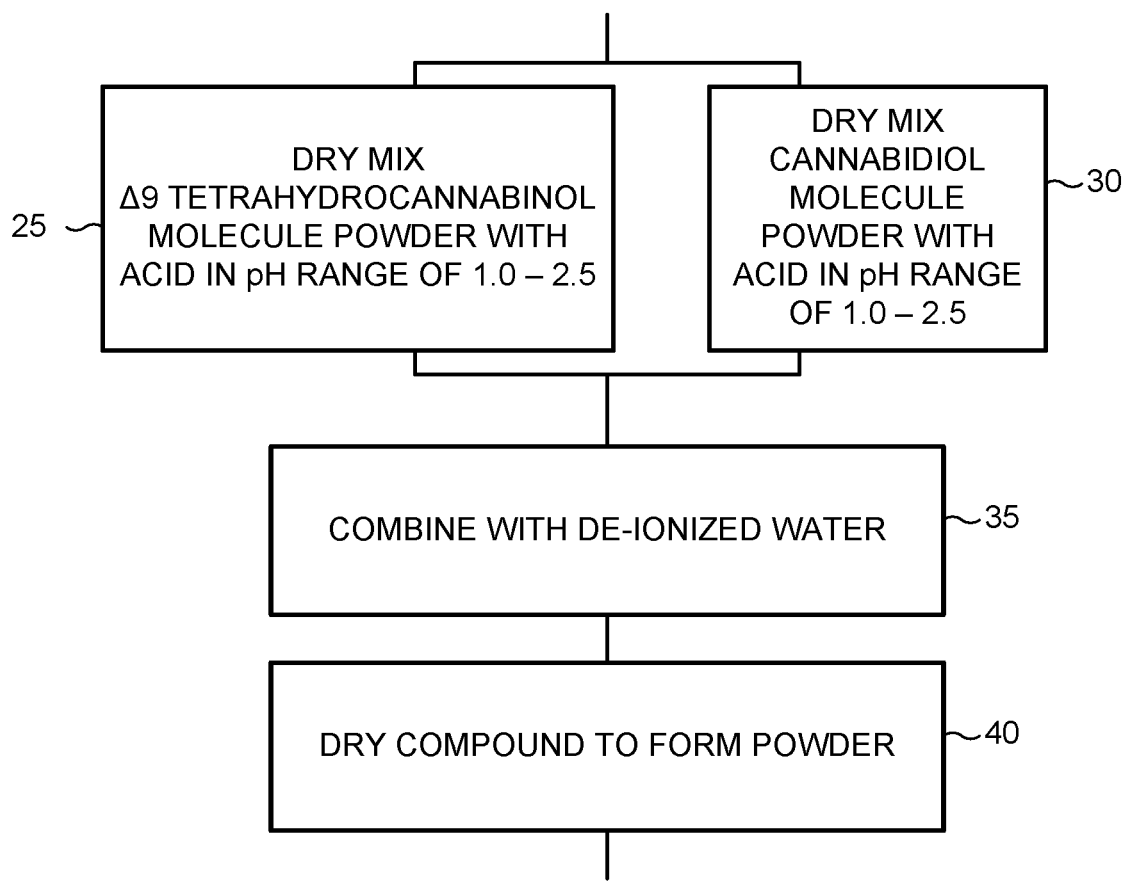
FIG. 2 is a flow diagram that depicts one alternative example method for etching the surface of a Cannabinoid molecule.

FIG. 2 is a flow diagram that depicts one alternative example method for etching the surface of a Cannabinoid molecule. This alternative example method includes a step wherein a THC molecule powder is dry mixed with an acid in the pH range of 1.0-2.5 (step 25). The present alternative example method further comprises a step wherein a CBD molecule powder is dry mixed with an acid in the pH range of 1.0-2.5. It should be appreciated, that Citric acid, Ascorbic acid, and a number of other acids commonly lie within these ranges. It should further be appreciated, that this low pH range allows for etching of the Cannabinoid molecule, while not being too harsh to human skin when the resulting bath bomb is used by the user. Ascorbic acid, necessary for the hydroxylation of proline to hydroxyproline in the production of collagen in all tissues including the vessel walls, complements as one of the requisite small molecules in the compositions of the present composition. This further enhances absorption.

FIG. 2 also depicts that this alternative example method further comprises a step wherein the resulting mixture is mixed with de-ionized water (step 35). It should be appreciated, that mixing the acid powder and the Cannabinoid molecule powder together in de-ionized water provides an opportunity for the acid powder and the Cannabinoid molecule powder to effectively rub together. This allows for more efficient etching of the Cannabinoid molecule and allows the Cannabinoid molecule and the acid to sit more closely together. This produces enhanced pharmacological properties.

FIG. 2 further depicts that this alternative example method also includes a step wherein the resulting compound is dried to form a powder (step 40). It should be appreciated, that the amount of moisture in a bath bomb must be strictly controlled to prevent the Sodium Bicarbonate powder and Citric acid powder from prematurely reacting. Further, the resulting acid-Cannabinoid molecule mixture needs to be dried into a powder so that it can be mixed with the other ingredients presented herein to form a Cannabinoid molecule bath bomb. It should be appreciated that there are number of ways to dry the wet mix of deionized water and acid-Cannabinoid molecule mixture into a dry powder. According to various illustrative use cases, the acid-Cannabinoid molecule mixture is dried using a spray drying method, wherein the wet mix is broken down into small droplets and then a heat source is applied. According to various other illustrative use cases, the acid-Cannabinoid molecule mixture is dried using a freeze-drying method, wherein the wet mix is fully frozen and then a deep vacuum is applied.

Figure 3:
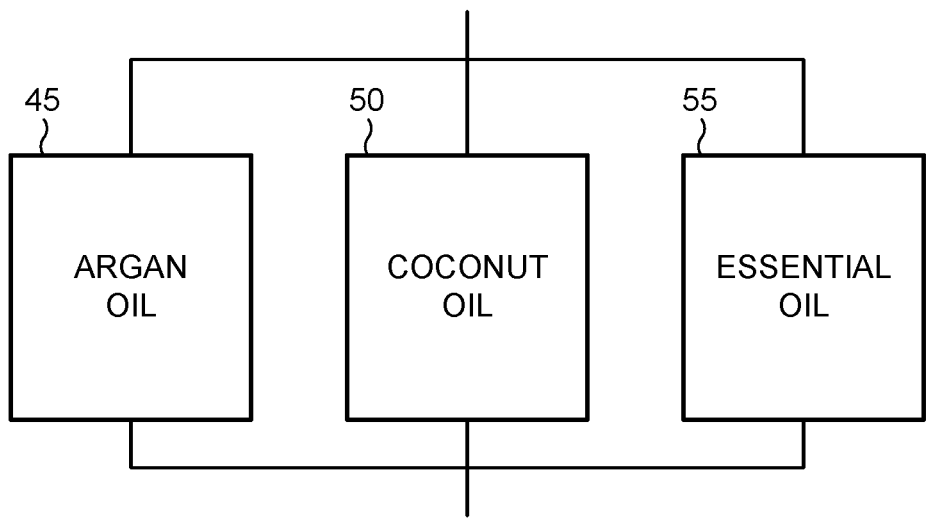
FIG. 3 is a flow diagram that depicts one alternative example method for a viscous binder.

FIG. 3 is a flow diagram that depicts one alternative example method for a viscous binder. This alternative example method includes a step wherein a viscous binder comprises at least one of Argan oil (step 45), Coconut oil (step 50), and essential oil (step 55). It should be appreciated that one or all of these viscous binders can be used together with the dry ingredients, presented elsewhere herein, to allow a Cannabinoid molecule bath bomb to be formed. It should further be appreciated, that a powder would be inconvenient for the user because it would require measuring and consistency, whereas a formed bath bomb is more convenient for the user because it allows simple application and consistent results.

Figure 4:
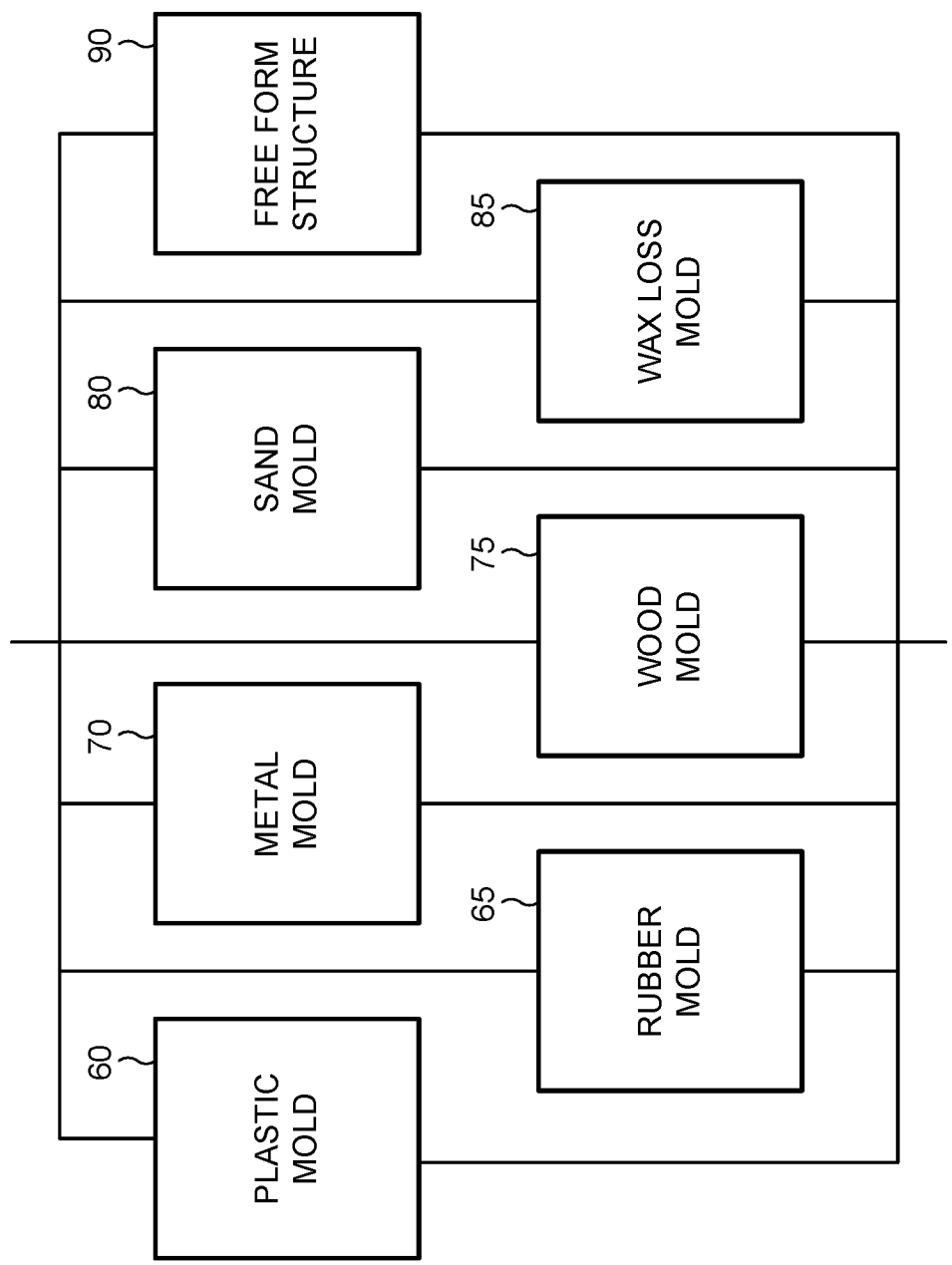
FIG. 4 is a flow diagram that depicts one alternative example method for drying to form a bath bomb.

FIG. 4 is a flow diagram that depicts one alternative example method for drying to form a bath bomb. This alternative example method includes a step wherein the resulting mixture is dried in at least one of a plastic mold (step 60), a rubber mold (step 65), a metal mold (step 70), a wood mold (step 75), a sand mold (step 80), a wax loss mold (step 85), and a free form structure (step 90). It should be appreciated, that forming the Cannabinoid molecule bath bomb into a consistent shape allows for ease-of-use by the user, consistent branding, packaging of the Cannabinoid molecule bath bomb, aesthetics, and other valuable goals.

Figure 5:
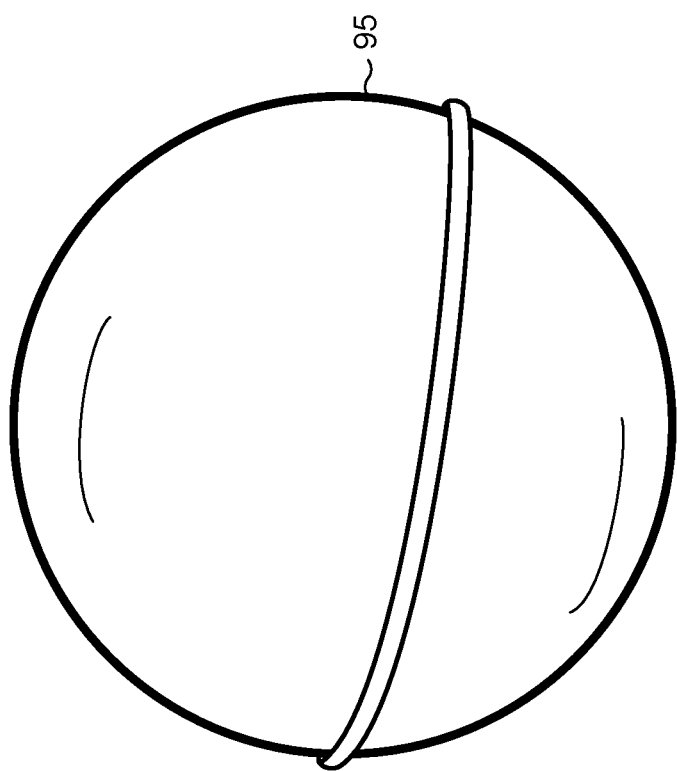
FIG. 5 is a pictorial representation of a formed bath bomb.

FIG. 5 is a pictorial representation of a formed bath bomb. In this alternative example method the bath bomb 95 is formed into a sphere. According to various illustrative use cases the Cannabinoid molecule bath bomb can be formed into a sphere 95; a figurative shape such as a unicorn head, cupcake, heart or snowflake; or a polyhedron.

Figure 6:
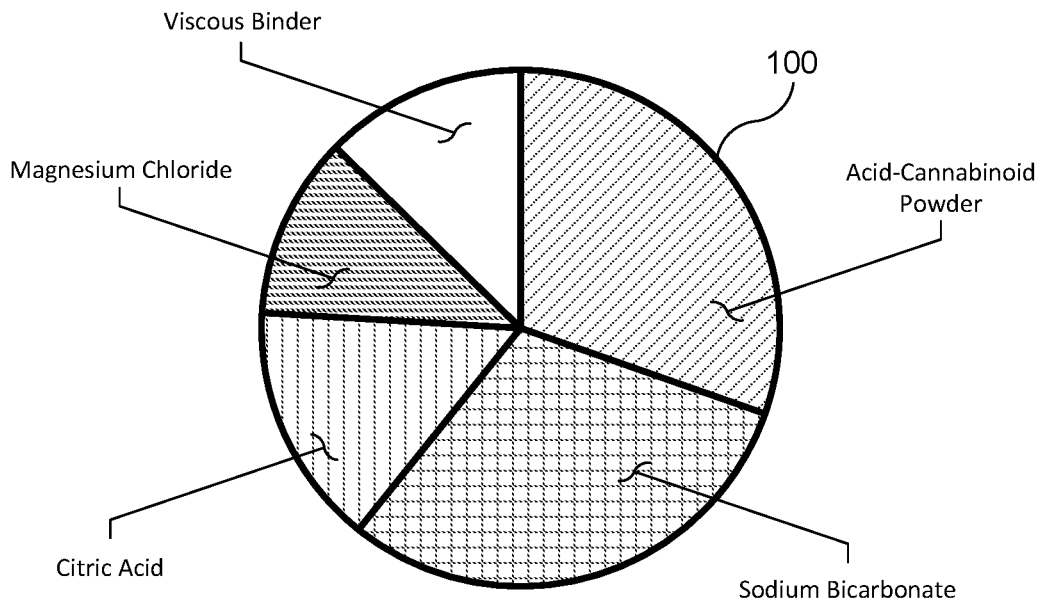
FIG. 6 is a pictorial representation that depicts one example embodiment of the material composition of a Cannabinoid molecule bath bomb with a higher acid-Cannabinoid powder concentration.

FIG. 6 is a pictorial representation that depicts one example embodiment of the material composition of a Cannabinoid molecule bath bomb with a higher acid-Cannabinoid powder concentration. According to one alternative example embodiment 100, an acid-Cannabinoid powder comprises 1 ounce of the composition. Additionally, this alternative example embodiment includes a Sodium Bicarbonate powder that comprises 1 times as much of the composition as the acid-Cannabinoid powder. Further, according to this alternative example embodiment, a Citric acid powder comprises 0.5 times as much of the composition as the acid-Cannabinoid powder. This alternative example embodiment further includes a Magnesium Chloride that comprises 0.375 times as much of the composition as the acid-Cannabinoid molecule powder. Further, according this alternative example embodiment, a viscous binder comprises 1.66 times as much of the composition as the acid-Cannabinoid powder.

Figure 7:
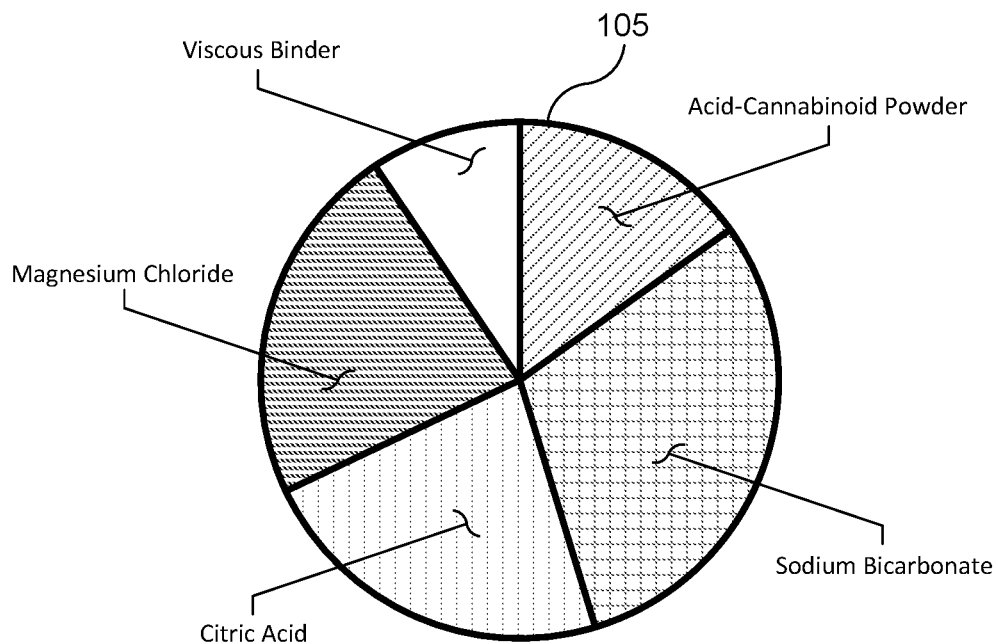
FIG. 7 is a pictorial representation that depicts one example embodiment of the material composition of a Cannabinoid molecule bath bomb with a lower acid-Cannabinoid powder concentration.

FIG. 7 is a pictorial representation that depicts one example embodiment of the material composition of a Cannabinoid molecule bath bomb with a lower acid-Cannabinoid powder concentration. According to this alternative example embodiment 105, an acid-Cannabinoid powder comprises 10 ounces of the composition. Further, according this alternative example embodiment a Sodium Bicarbonate powder comprises 2 times as much of the composition as the acid-Cannabinoid powder. This alternative example embodiment further includes a Citric acid powder that comprises 1.5 times as much of the composition as the acid-Cannabinoid molecule powder. Additionally, this alternative example embodiment includes a Magnesium Chloride that comprises 1.5 times as much of the composition as the acid-Cannabinoid molecule powder. Further, according this alternative example embodiment a viscous binder comprises 0.25 times as much of the composition as the acid-Cannabinoid molecule powder.

In one embodiment of the material composition of a Cannabinoid molecule bath bomb, the bath bomb comprises 1-10 ounces (28.35 g-283.5 g) of an acid-etched cannabinoid powder, sodium bicarbonate in an amount from 1-2 times the weight of the acid-etched cannabinoid powder, citric acid powder in an amount from 0.5-1.5 times the weight of the acid-etched cannabinoid powder, magnesium chloride in an amount from 0.375-1.5 times the weight of the acid-etched cannabinoid powder, and a viscous binder in an amount from 0.25-1.66 times the weight of the acid-etched cannabinoid powder.

What is claimed is:

1. A method of making a cannabinoid-containing bath bomb comprising:
   etching a surface of at least one of a Δ9 tetrahydrocannabinol (THC) powder and a cannabidiol (CBD) powder by:
   dry mixing at least one of a Δ9 THC powder and a CBD powder with at least one of citric acid powder and ascorbic acid powder in a pH range of 1.0 to 2.5;
   combining the resulting mixture with de-ionized water and mixing; and
   drying to form an acid-etched cannabinoid powder;
   combining the acid-etched cannabinoid powder with sodium bicarbonate, citric acid, magnesium chloride, and a viscous binder; and
   drying the resulting mixture to form a bath bomb.

2. The method of claim 1, wherein the viscous binder comprises at least one of argan oil, coconut oil, and essential oil.

3. The method of claim 1, wherein drying the resulting mixture to form the bath bomb comprises:
   drying the resulting mixture in at least one of a plastic mold, a rubber mold, a metal mold, a wood mold, a sand mold, a wax loss mold, and a free form structure.

4. A bath bomb prepared according to claim 1, comprising:
   28.35 g-283.5 g of an acid-etched cannabinoid powder;
   sodium bicarbonate, from 1-2 times the weight of the acid-etched cannabinoid powder;
   citric acid powder, from 0.5-1.5 times the weight of the acid-etched cannabinoid powder;
   magnesium chloride, from 0.375-1.5 times the weight of the acid-etched cannabinoid powder; and
   a viscous binder, from 0.25-1.66 times the weight of the acid-etched cannabinoid powder.

* * * * *